(12) United States Patent
Janicki

(10) Patent No.: US 9,193,022 B1
(45) Date of Patent: Nov. 24, 2015

(54) DRILL BIT SYSTEM AND ASSEMBLY

(75) Inventor: Thomas I. Janicki, Cleveland, OH (US)

(73) Assignee: Artosto, LLC, Cleveland, OH (US)

( * ) Notice: Subject to any disclaimer, the term of this patent is extended or adjusted under 35 U.S.C. 154(b) by 404 days.

(21) Appl. No.: 13/352,109

(22) Filed: Jan. 17, 2012

Related U.S. Application Data

(60) Provisional application No. 61/432,648, filed on Jan. 14, 2011.

(51) Int. Cl.
B23Q 15/007 (2006.01)
B23Q 17/09 (2006.01)

(52) U.S. Cl.
CPC .......... *B23Q 15/007* (2013.01); *B23Q 17/0952* (2013.01)

(58) Field of Classification Search
CPC .... B23Q 15/007; B23Q 15/013; B23Q 15/14; B23Q 17/0952
USPC ......... 408/5, 6, 7, 8, 9, 10, 11, 12, 14, 15, 16, 408/226; 407/53, 54; 362/119, 120; 409/186, 187, 188; 700/175
See application file for complete search history.

(56) References Cited

U.S. PATENT DOCUMENTS

| | | | |
|---|---|---|---|
| 3,310,796 A * | 3/1967 | Sanders | 340/671 |
| 4,420,253 A * | 12/1983 | Pryor | 356/237.1 |
| 4,692,611 A | 9/1987 | Hoogenboom | |
| 6,419,484 B1 | 7/2002 | DaSilva et al. | |
| 6,481,939 B1 * | 11/2002 | Gillespie et al. | 409/131 |
| 6,719,692 B2 * | 4/2004 | Kleffner et al. | 600/437 |
| 7,257,879 B1 * | 8/2007 | Jancso et al. | 29/566 |
| 2010/0078414 A1 | 4/2010 | Perry et al. | |
| 2011/0180521 A1 * | 7/2011 | Quitter et al. | 219/121.73 |

FOREIGN PATENT DOCUMENTS

EP 1741394 A1 10/2007

* cited by examiner

Primary Examiner — Sunil K Singh
Assistant Examiner — Alan Snyder
(74) Attorney, Agent, or Firm — Brennan, Manna & Diamond, LLC

(57) ABSTRACT

A drill bit is disclosed including a rigid cutting tool elongated along a central axis having opposed sides, where one side includes a cutting edge and an opposing side includes a shank for selective engagement with a drill chuck. The drill bit includes a first light path capable of communicating light between the shank side of the drill bit and the cutting edge side of the drill bit. The drill bit may be used with a breach assessment mechanism including a light source configured to provide selective illumination along the light path and a light sensor. Processor logic may be programmed to assess signals from the light sensor indicative of reflected light from a cutting surface contacting the cutting side of the drill bit.

20 Claims, 5 Drawing Sheets

DRILL BIT SYSTEM AND ASSEMBLY

RELATED APPLICATIONS

This application claims priority to U.S. Provisional Application No. 61/432,648 filed Jan. 14, 2011.

SUMMARY

In one embodiment a system comprises of two elements: a reusable drill bit and light generation and detection logic to assess the reflected light intensity emanating from the drill bit. The system uses a measurement of the intensity of the reflected light of any desired wave length or configuration as it passes through the drill bit and is reflected of the interface present at the leading edge of the drill bit. Alternately, the system compares intensities of a plurality of reflections with each other or reflections and the source light or combinations. The initiation of the final breach of the drilled item or cutting surface is associated with decrease in the intensity of the reflected light.

One aspect of an exemplary drill bit is an inlaid "Y" bifurcated light-guide complex. The distal end of the light-guide complex is exposed at or near the leading edge of the drill bit. The light-guide travels from the distal portion of the drill bit toward its proximal aspect and at convenient location it may bifurcate into two separate light guides. After the bifurcation both of those proximal light-guides terminate at the lateral aspect of the proximal portion of the drill bit. Light acquisition and reflected light measurement properties may be enhanced by specific termination lenses incorporated into the light-guides at the lateral aspect of drill bit. One of the proximal light-guides captures the light from an external light source disposed within a light generation and detection logic or as used interchangeably, a breach assessment mechanism and transmits the light to the distal end of the drill bit. The other proximal light-guide captures the reflected light from the tip of the drill bit and transmits it via Y junction to its exit point at the lateral aspect of the proximal portion of the drill bit. That reflected light is then captured and measured by a sensor located within the breach assessment mechanism.

In one embodiment a groove may be manufactured in the drill bit to house or contain the light guide. Such groove may contain sparingly dispersed pits that provide additional anchor for the light guide, thus preventing it from being dislodged by mechanical forces acting upon the leading edge of the drill bit. Additional features placed at the leading edge of the drill bit may include a breach sensor such as a hard, optically transmissive crystal of the hardness similar or exceeding a hardness of the material from which the drill bit is manufactured. In one embodiment, a diamond or sapphire tip may be employed. The drill bit may also be equipped with a bit stop to permit proper depth into the drill chuck to allow alignment between the lenses or optical path between the bit and light generation and detection logic. In one embodiment, a light acquisition lens and reflected light lens on the drill bit and/or corresponding lenses associated with the light source and light sensor in the light generation and detection mechanism may improve optical communication between the bit and the light generation and detection mechanism.

Light generation and detection logic may be configured as a detachable logic complex providing light for the drill bit and capturing and analyzing reflected light from the drill bit. The logic may also include an indicator, such as visual (light) or acoustic (noise), of the impending breach of the drilled material. The logic may also include a self-contained power source (batteries) or it can use the power provided by the drill unit itself. Light generation and detection logic may also be equipped with appropriate hardware and software to enable it to analyze reflected light intensity and provide a user with an appropriate indication. Light generation and detection logic may attach to the drill housing with an arm positioned such as to align the optical paths.

When the drill is activated, light from the light source may be routed to the optical path of the drill bit by an appropriate optics, for example, fiber and lens and an intensity of the light reflected at the leading or cutting edge of the drill bit may be assessed by returning reflected light to a light sensor within light generation and detection logic. As the drilling progresses the distance between the leading or cutting edge of the drill bit and the drilled material is zero or near zero, thus producing the highest intensity of the reflected light. The moment the drill bit starts penetrating outer "shell" of the drilled material, the distance to the reflective elements, that is, the drilled material serving as reflective medium increases. That in turn drops intensity of the light reflected and that in turn lowers the signal produced by the light sensor in light generation and detection logic. Appropriate ranges of such drop of the intensity of the reflected light are input into the logic unit to trigger, for example, a light or an audio signal alerting the drill user to the impending breach of the drilled material. Additionally variety of colored filters can be used to enhance application of the drill bit to different materials.

BRIEF DESCRIPTION OF THE DRAWINGS

The accompanying drawings, which are incorporated in and constitute a part of the specification, illustrate various example systems, methods, and so on that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION OF THE DRAWINGS

"Drill bit", as used herein, includes but is not limited to all varieties of bits, right hand and left hand bits, twist bits, masonry bits, spur point bits, bullet point bits, countersink bits, glass or tile bits, reamers, flat wood bits, spade bits, hole saws, burr hole bit, forstner bits, wood auger bits and other bits now known or later developed.

"Logic", as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), a programmed logic device, memory device containing instructions, or the like. Logic may also be fully embodied as software.

"Signal", as used herein, includes but is not limited to one or more electrical or optical signals, analog or digital signals, one or more computer or processor instructions, messages, a bit or bit stream, or other means that can be received, transmitted, and/or detected.

"Software", as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

Figure 1:
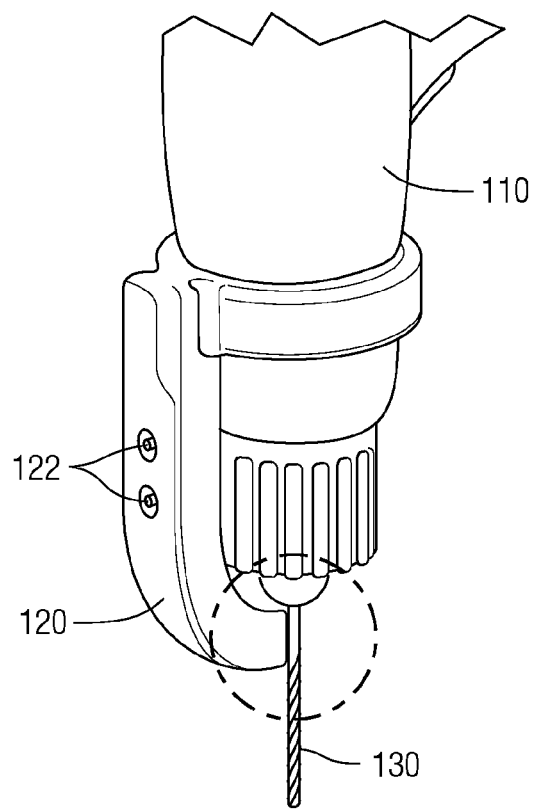
FIG. 1 is a perspective view of a system according to an embodiment of the disclosure.

FIG. 1 shows a perspective view of an embodiment of a drill 110 and a connected light generation and detection logic 120 closely arranged with a drill bit 130. Light generation and detection logic 120 is illustrated with LED displays 122 to alert a user to a breach or about to breach cutting surface as more completely discussed below.

Figure 1A:
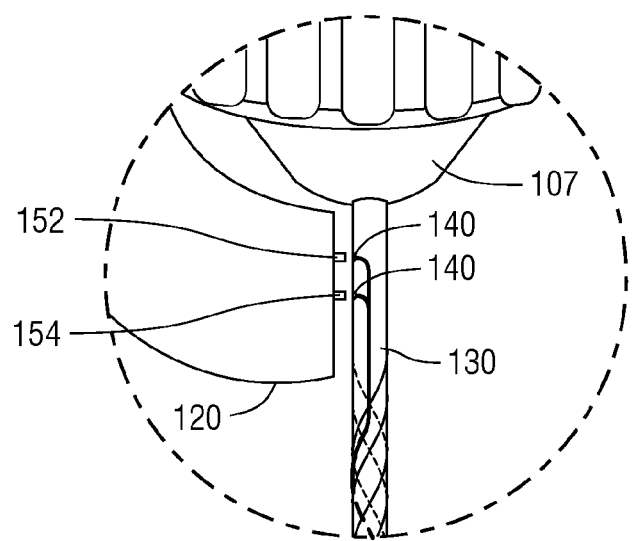
FIG. 1A is an enlarged elemental view of FIG. 1.

FIG. 1A shows an embodiment of the alignment between lateral light guide terminations 140 on a shank side of the drill bit 130 and a terminal portion of light sensor path 152 and light source path 154 in the light generation and detection logic 120.

Figures 2, 2A:
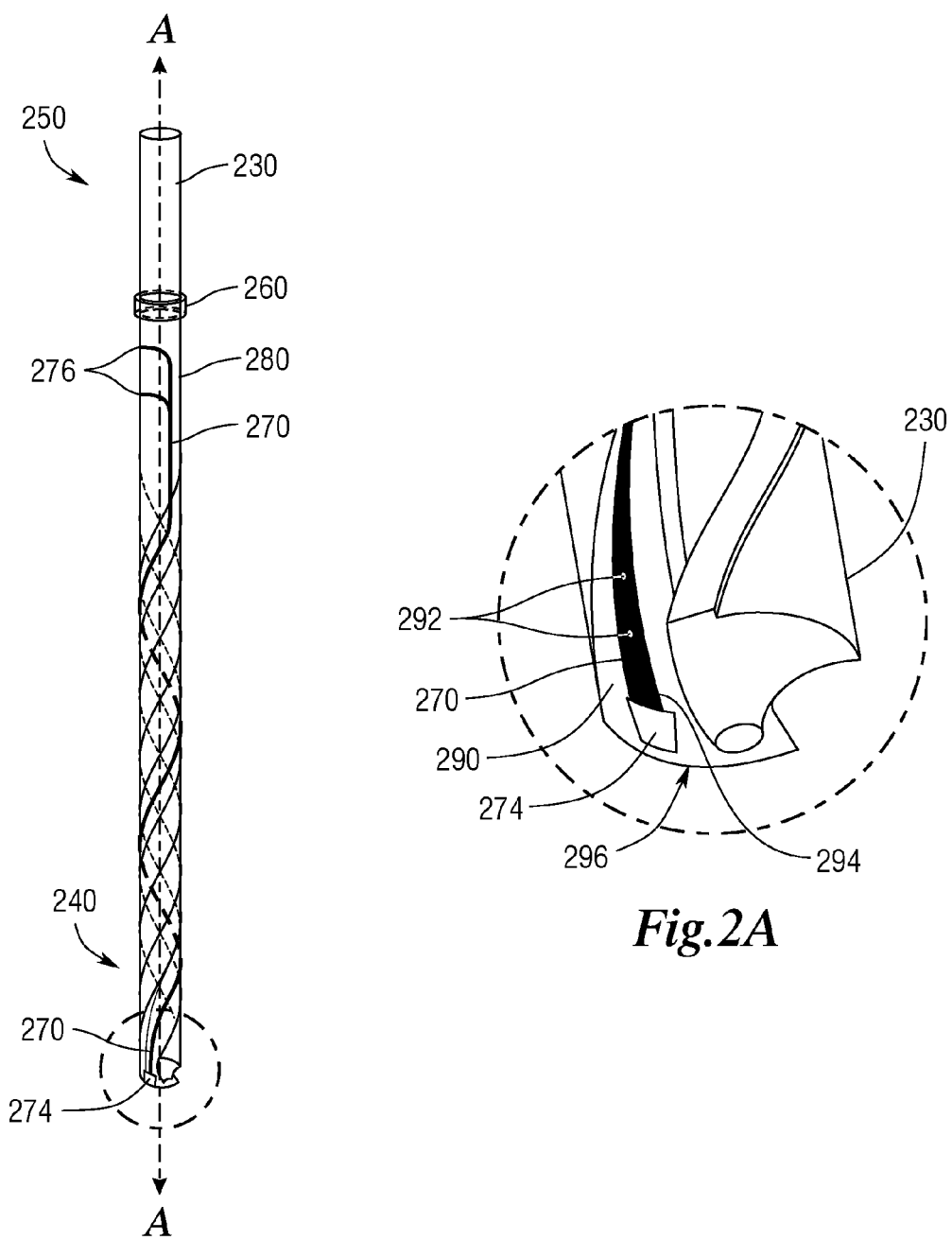
FIG. 2 is a perspective view of a drill bit according to an embodiment of the disclosure.
FIG. 2A is an enlarged elemental view of FIG. 2.

FIG. 2 shows a perspective view of an exemplary drill bit 230 or cutting tool, elongated along a central axis A. A distal side includes cutting edges 240 and an opposite side may be smooth, cylindrical, or shaped to form a shank 250 for engagement with the chuck of a drill (not shown). Drill bit 230 may include a bit stop 260 to ensure proper depth of the shank within the chuck to ensure alignment of drill bit light path(s) on the shank side of the drill bit and corresponding light path(s) in the light generation and detection logic 120. Drill bit 230 also includes a light path 270. Light path 270 provides a path for optical communication between a distal side terminus ending in a hardened breach sensor 274 and proximal termination(s) 276 disposed proximately toward the shank 250 side of the bit. As used in describing a light path "between" components, the use is intended to include one-way light travel from a first component to a second component, one way light travel from the second component to the first component, and round trip travel between components. In the illustrated embodiment, the drill bit 230 further includes a Y— split 280 splitting the light path into the two, off axis A light path terminations 276. In an alternate embodiment, the drill bit 230 may include two or more light paths, for example, one in each cutting edge and two or more Y-splits and terminations for communication with the light generation and detection logic. In another embodiment, the light path may be disposed substantially along the central axis A as opposed to along or inside the cutting channels as illustrated.

FIG. 2B illustrates a detail of one embodiment of the leading edge of the exemplary drill bit 230 from FIG. 2. The drill bit may include a light path 270 configured as a transparent light guide located within a flute or grove 290 forming a cutting edge in the drill bit 230. The grove 290 may include spherical pits 292 to increase mechanical stability of the light path 270 within the grove 290. The distal aspect of the light path 270 within the drill bit 230 contains a hardened breach sensor 274 in the form of a crystal extending between leading edge 294 of the light path 270 and the distal termination point 296 of the light path 270 at or near the face or point of the drill bit 230.

Figure 3:
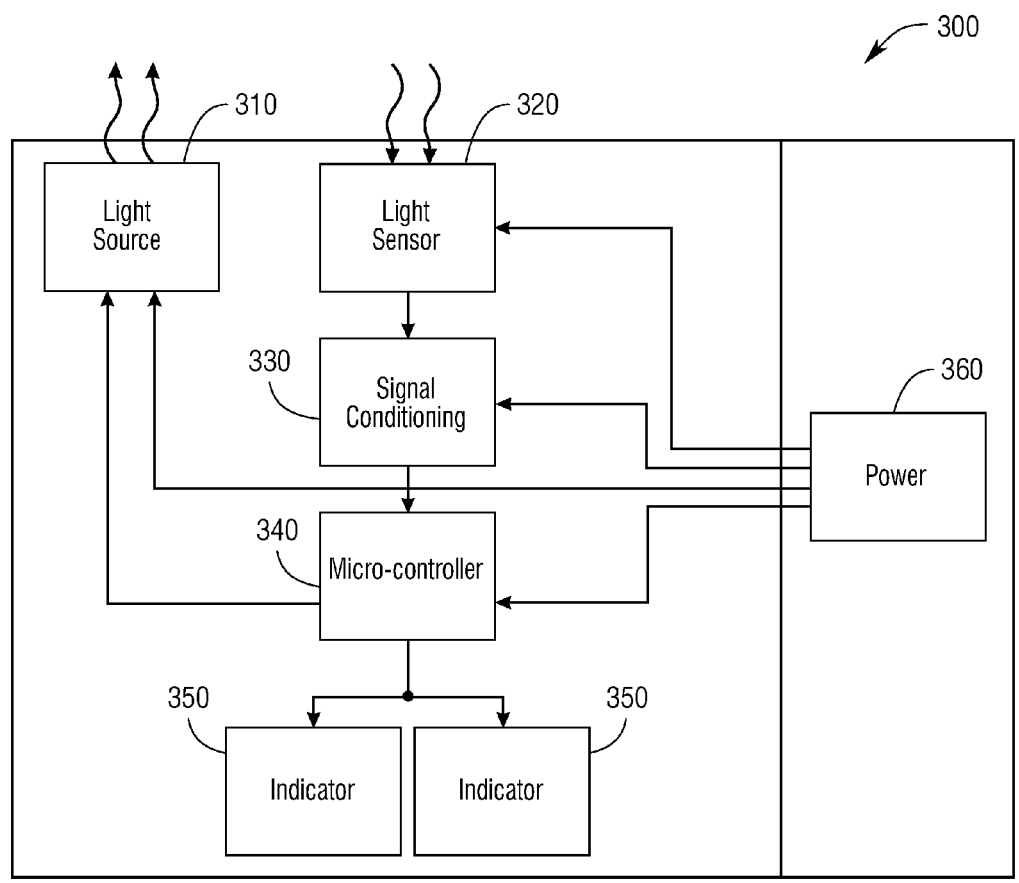
FIG. 3 is a block diagram of light generation and detection logic according to an embodiment of the disclosure.

FIG. 3 illustrates a functional block diagram of an exemplary breach assessment mechanism 300, including a light source 310, a light sensor 320, signal conditioning circuitry 330, control logic 340, indicators 350 and a power source 360. A compact electrically driven light source 310 emitting adequate radiant flux to allow measurements of reflected light by the light sensor 320. In one embodiment, light source 310 comprises a low-power white-light broadband visible spectrum LED with a molded plastic lens. However the light source 310 may be chosen to enhance measurement of particular drilled materials. Possible light source 310 optical parameters may include narrow or broadband spectral content from the UV to infrared region, linear or circular polarization, coherent or incoherent light, and intensity pulsing or modulation. These characteristics are readily available with off-the-shelf light sources such as LEDs, laser diodes, incandescent bulbs, and discharge lamps, combined with the use of optional wavelength converting phosphors and optical filters. The light source 310 may contain a lens for efficient optical coupling between the light source 310 and the drill bit (not shown). Light pulsing may be used to reduce power consumption, and light modulation may reduce ambient light interference. The light source 310 may be pulsed or modulated by a digital or analog control signal from control logic 340, and the light source 310 may receive power from the control logic 340 control signal or power source 360.

Light sensor 320 receives reflected light from the drill bit (not shown) and may convert the reflected light to an electrical signal. In one embodiment, the light sensor 320 is spectrally matched to the light source 310 and is sensitive to optical wavelengths of interest. The response time is selected to be adequate to detect light intensity variations during the rotation of the drill bit. In one embodiment, light sensor 320 comprises a photodiode with a molded plastic lens. Other suitable substitutes may be selected based on cost, sensitivity, and response time, and substitutes may include a light dependent resistor, photovoltaic cell, phototransistor, CCD, microbolometer, or other electro-optical sensor matched to the light source 310. Optical filters may optionally be applied to the light sensor 320 to restrict the measurement spectrum or polarization, to reduce interference or increase measurement sensitivity. The light sensor 320 may contain a lens for efficient optical coupling between the drill bit (not shown) and light sensor 320. The light sensor 320 may use power from the control logic 340 or power source 360.

Signal conditioning circuitry 330 may include passive or active circuitry to convert the light sensor 320 electrical output to a suitable voltage range for sampling by the control logic 340 for example, in analog-to-digital converter circuitry. Additionally, frequency selective filtering may be applied to reduce unwanted noise and perform anti-aliasing before analog to digital conversion. In one embodiment, signal conditioning circuitry 330 suitable for a photodiode light sensor comprises a transimpedance amplifier circuit with a low pass filter characteristic for antialiasing light. Other light sensors have well known application circuits that may be implemented conventionally. System performance may allow a simple and lowest cost resistor-capacitor (RC) signal conditioning circuitry. The signal conditioning circuitry 330 may use power from power source 360.

Control logic 340 may include a single-chip microcontroller with integrated program memory, RAM, timers, and an analog-to-digital converter that implements programmed or hardwired logic to control the light generation and detection logic. The control logic 340 samples the signal-conditioned signal from light sensor 320, executes an algorithm to analyze the reflected light signal from the drill bit, and outputs system and drill bit status information to the indicators 350. Individually or in combination, light sensor 320, signal conditioning circuitry 330 if any, and control logic 340 may be referred to as a detector to identify when the drill bit breaches a drilled layer. The control logic 340 may send a digital or analog control signal to light source 310 to modulate or pulse the light intensity in the case of an analog control signal, Control logic 340 may contain a digital to analog converter. Control logic 340 may receive power from power source 360 and may control power functions including power saving mode and energy storage (e.g. battery charging). Control logic 340 may be highly integrated to include some or all of the light generation and detection logic components, or may use external components for individual features.

The indicator(s) 350 displays the drill bit system state to the drill operator. Exemplary system states may include indication of power on/off, system ready, and drill bit final breach. One embodiment is two indicator LEDs 350 to visually alert the operator, for example one of which to indicate system power and readiness and the other to indicate drill bit final breach. Alternatively, the indicator may include an audible indicator such as a beep, tone, speech, or some other audible signaling method, or a visual indicator that varies intensity, color, shape, text, or symbols to indicate the system state.

The power source 360 for a breach assessment mechanism 300 may include any variety of power now known or later developed. For example, suitable power requirements can be met from an internal battery, the drill's power source, or an external power source. In one embodiment, the breach assessment mechanism 300 uses an internal battery and an external power jack that overrides internal battery power. The breach assessment mechanism 300 may have on-board energy storage in the form of a rechargeable or non-rechargeable battery or other energy storage device, and control of energy management may be performed by control logic 340. The power may be supplied using electrically conductive wires, wireless power transfer using inductive. RF, or optical power transfer, or other methods.

The breach assessment mechanism 300 may be contained and protected by a casing, for example positioned in the drill housing to optically align with the drill bit. In other embodiments, the casing may be supplied in, but is not limited to, a detachable enclosure that may be added to any third party drill, a molded enclosure on the drill bit shank, or a drill chuck with integrated breach assessment mechanism that fits into a drill chuck. The enclosure is preferably plastic for low weight, low cost, and durability. If needed in a particular implementation, the enclosure may include a means of battery access.

Figure 4:
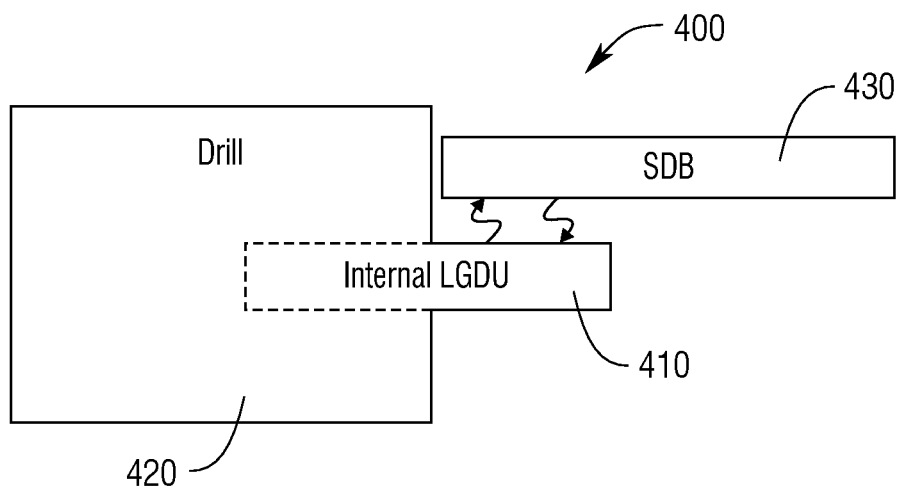
FIG. 4 is a block diagram of an embodiment of light generation and detection logic integral to the drill.

FIG. 4 illustrates one embodiment of a drill bit system 400. In the illustrated embodiment, breach assessment mechanism 410 is integral to the body of a drill 420 and receives power from the drill power source. The breach assessment mechanism 410 is positioned within or formed integrally with the drill body to optically align with a drill bit 430. The drill may be used with conventional drill bits and optical drill bits as described herein. The system and any status indicator may be disposed at a convenient location on the drill body.

Figure 5:
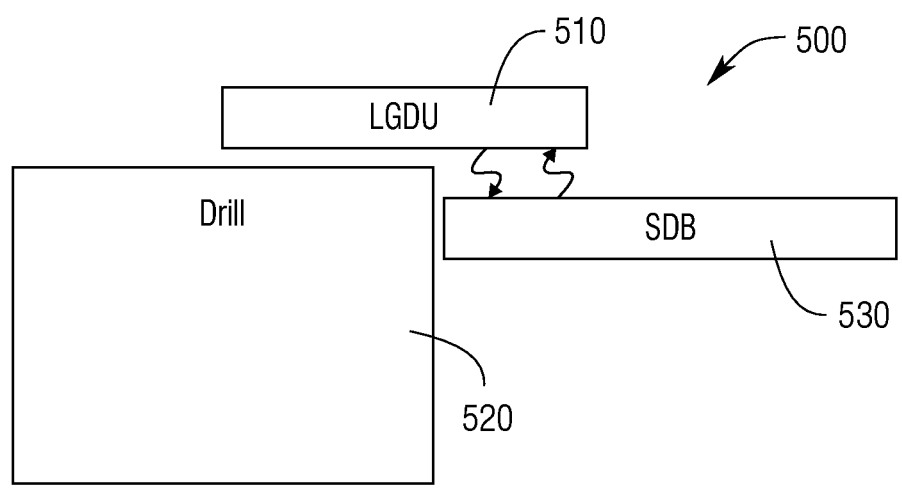
FIG. 5 is a block diagram of an embodiment of light generation and detection logic affixed to an existing drill.

FIG. 5 illustrates another embodiment of a drill bit system 500. In the illustrated embodiment, breach assessment mechanism 510 is connected externally to an existing drill 520. The breach assessment mechanism 510 may include internal energy storage such as a battery and an external power jack to supplement internal power with power from the drill or a wall adapter. The breach assessment mechanism 510 is positioned on the outside of the drill body to optically align with a drill bit 530. The breach assessment mechanism 510 enclosure may contain the status indicator.

Figure 6:
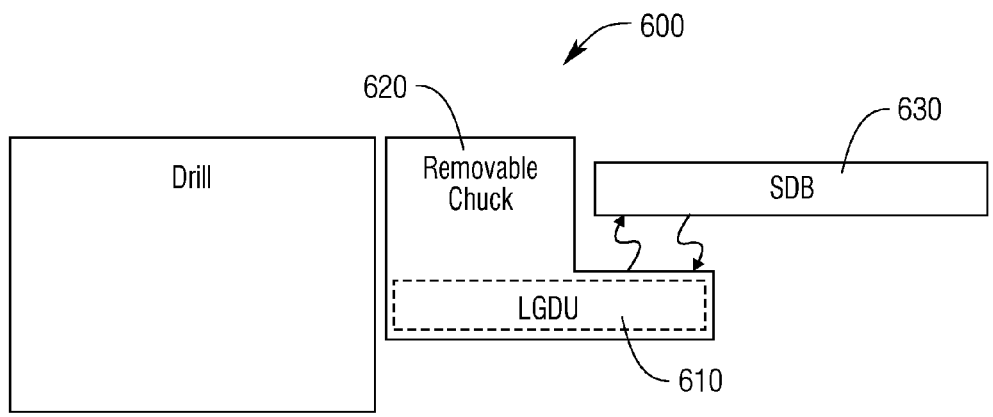
FIG. 6 is a block diagram of an embodiment of light generation and detection logic integrated into a removable drill chuck.

FIG. 6 illustrates another embodiment of a drill bit system 600. In the illustrated embodiment, breach assessment mechanism 610 is integral or at least partially integral to a drill chuck 620 capable of holding a drill bit 630. The breach assessment mechanism 610 may draw power from either an internal energy storage such as a battery, or the drill power source or both. The status indicator should be noticeable in all directions, so a light guide or sound guide may be used to distribute light or sound respectively in all directions.

Figure 7:
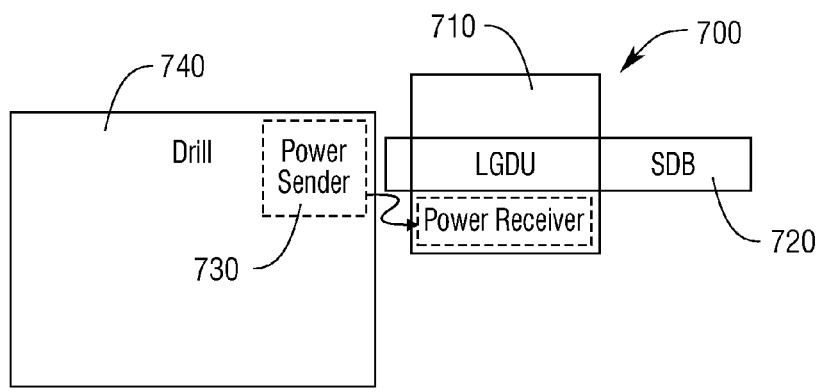
FIG. 7 is a block diagram of an embodiment of light generation and detection logic integrated onto the drill bit and wireless power transfer.

FIG. 7 illustrates another embodiment of a drill bit system 700. In the illustrated embodiment, breach assessment mechanism 710 is integral to a drill bit 720. The breach assessment mechanism 710 and drill bit 720 assembly may have an internal energy source such as a battery but preferably employ a wireless power from a power sender unit 730 associated with the drill 740. Wireless power transfer can be implemented over short distances for example using inductively coupled coils or other methods. The status indicator should be noticeable in all directions, so a light band surrounding the breach assessment mechanism 710 or drill bit 720 may be used to distribute light or alternatively sound may be used.

While the systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicants' general inventive concept. For example, the light assisted breach assessment teachings herein may be applied to other arts where determining penetration is desirable. One area where such a determination may be used is in the medical arts, for example, in placing an epidural needle. Another area where such a determination may be used is in the explosive fusing arts, for example, in delaying a detonation until ordinance has breached a fortification. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

As used herein, "connection" or "connected" means both directly, that is, without other intervening elements or components, and indirectly, that is, with another component or components arranged between the items identified or described as being connected. To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the claims (e.g., A or B) it is intended to mean "A or B or both". When the applicants intend to indicate "only A or B but not both" then the term "only A or B but not both" will be employed. Similarly, when the applicants intend to indicate "one and only one" of A, B, or C, the applicants will employ the phrase "one and only one". Thus, use of the term "or" herein is the inclusive, and not the exclusive use. See, Bryan A. Garner, A Dictionary of Modern Legal Usage 624 (2d. Ed. 1995).

I claim:

1. A drill assembly comprising:
   a drill;
   a drill bit including a cutting side and an opposing side selectively disposable in a chuck attached to the drill, where the drill bit comprises a light path extending between the cutting side and the opposing side; and
   a breach assessment mechanism in operative communication with the drill bit, where a breach sensor disposed on the cutting side of the drill bit communicates with a detector to identify when the drill bit breaches a drilled layer.

2. The drill assembly as set forth in claim 1, where the breach sensor comprises a hard optically transmissive crystal disposed adjacent to a distal tip on the cutting side of the drill bit, where the crystal terminates the light path.

3. The drill assembly as set forth in claim 1, where the breach assessment mechanism comprises a light source in optical communication with the light path.

4. The drill assembly as set forth in claim 1, where the detector comprises a light sensor in optical communication with the light path.

5. The drill assembly as set forth in claim 1, where the detector comprises a light sensor, the breach assessment mechanism further comprising:
   a light source; and
   processor logic programmed to control power to the light source, where when on the light source provides illumination along a light path extending between the cutting side and the opposing side of the drill bit and the processor logic further programmed to assess signals from the light sensor indicative of reflected light from a cutting surface adjacent the cutting side of the drill bit.

6. The drill assembly as set forth in claim 1, where the breach assessment mechanism comprises an indicator to alert an operator when the drill bit breaches a drilled layer.

7. The drill assembly as set forth in claim 5, where the processor logic is programmed to provide an alert when the reflected light is reduced below a threshold.

8. The drill assembly as set forth in claim 1, where the breach assessment mechanism comprises a power source.

9. A drill bit comprising:
   a rigid cutting tool elongated along a central axis having opposed sides, where one side includes a cutting edge and an opposing side includes a shank for selective engagement with a drill chuck; and
   a first light path capable of communicating light between the shank and the cutting edge, where the first light path includes an optically transmissive crystal at a terminal end on the cutting edge.

10. The drill bit as set forth in claim 9, where the at least one light path further comprises a Y-split disposed away from the cutting edge where the Y-split terminates in two light paths spaced from each other and disposed orthogonal to the central axis accessible on an exterior of the drill bit.

11. The drill bit as set forth in claim 9, further comprising a second light path independent of the at least one light path, the second light path being capable of communicating light between the shank and the cutting edge.

12. A machine comprising:
    a drill bit elongated along an axis having opposed sides, where one side includes an optically transmissive cutting edge and an opposing side includes a shank for selective engagement with a drill chuck, the drill bit further comprising at least one light path capable of communicating light from the shank side of the drill bit to the cutting edge side of the drill bit; and
    a breach assessment mechanism configured for optical communication with the light path where a distal termination point of the light path communicates reflected light from a cutting surface to a proximal termination of the light path.

13. The machine as set forth in claim 12, where the breach assessment mechanism comprises:
    a light source; and
    a light sensor;
    logic programmed to control the light source providing illumination along the at least one light path to the distal termination point and to receive signals from the light sensor corresponding to reflected light from the distal termination point;
    where the light sensor detects reflected light from the cutting surface.

14. The machine as set forth in claim 12, where the light path comprises a first optical path for communicating light to the cutting edge and a second optical path for communicating reflected light from the cutting edge.

15. The machine as set forth in claim 14, where the breach assessment mechanism comprises:
    a light source;
    a light sensor; and
    logic programmed to power the light source providing illumination along the first optical path to the distal termination point and to receive signals from the light sensor corresponding to reflected light received from the second optical path from the distal termination point.

16. The machine as set forth in claim 12, where the distal termination point comprises an optically transmissive sapphire tip.

17. A breach assessment mechanism configured for operative communication with a drill bit comprising:
    a light source configured to provide selective illumination along a light path extending between a breach sensor on a cutting side of the drill bit and a proximal side of the drill bit;
    a light sensor; and
    processor logic programmed to assess signals from the light sensor indicative of reflected light from a cutting surface contacting the cutting side of the drill bit.

18. The breach assessment mechanism as set forth in claim 17, where the breach assessment mechanism further comprises an indicator to indicate when the drill bit breaches a drilled layer.

19. The breach assessment mechanism as set forth in claim 17, where the processor logic is programmed to provide an indication when the reflected light is reduced below a threshold.

20. The breach assessment mechanism as set forth in claim 17, where the breach assessment mechanism comprises a power source.

* * * * *